(12) United States Patent
Lang et al.

(10) Patent No.: US 7,235,404 B2
(45) Date of Patent: Jun. 26, 2007

(54) CYANIDE-FREE LYTIC REAGENT COMPOSITION AND METHOD OF USE FOR HEMOGLOBIN AND WHITE BLOOD CELL MEASUREMENT

(75) Inventors: Russell F. Lang, Pembroke Pines, FL (US); Dennisse Parra-Diaz, Miami, FL (US); Luisa Oramas, Weston, FL (US); Barbara Murza, Miami, FL (US); Susana Maldonado, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 280 days.

(21) Appl. No.: 11/125,395

(22) Filed: May 4, 2005

(65) Prior Publication Data

US 2006/0263889 A1 Nov. 23, 2006

(51) Int. Cl.
*G01N 33/72* (2006.01)
*G01N 31/00* (2006.01)

(52) U.S. Cl. ............... 436/66; 436/8; 436/10; 436/17; 436/63; 436/164; 436/166; 436/174; 435/2; 252/408.1

(58) Field of Classification Search ............ 436/8, 436/10, 17, 63, 66, 164, 166, 174, 175, 179; 435/2; 252/408.1
See application file for complete search history.

(56) References Cited

U.S. PATENT DOCUMENTS

| | | | |
|---|---|---|---|
| 2,656,508 A | 10/1953 | Coulter | |
| 4,378,971 A * | 4/1983 | Schwartz | 436/66 |
| 4,485,175 A | 11/1984 | Ledis et al. | |
| 4,521,518 A | 6/1985 | Carter et al. | |
| 4,528,274 A | 7/1985 | Carter et al. | |
| 5,242,832 A | 9/1993 | Sakata | |
| 5,250,437 A * | 10/1993 | Toda et al. | 436/10 |
| 5,468,640 A * | 11/1995 | Benezra et al. | 436/66 |
| 5,612,223 A * | 3/1997 | Kim et al. | 436/17 |
| 5,763,280 A | 6/1998 | Li et al. | |
| 5,834,315 A * | 11/1998 | Riesgo et al. | 436/66 |
| 5,866,428 A | 2/1999 | Kim et al. | |
| 5,882,934 A | 3/1999 | Li et al. | |
| 5,935,857 A | 8/1999 | Riesgo et al. | |
| 5,958,781 A * | 9/1999 | Wong et al. | 436/63 |
| 6,706,526 B2 | 3/2004 | Lang et al. | |
| 6,740,527 B1 | 5/2004 | Wong et al. | |
| 6,890,756 B2 * | 5/2005 | Wu | 436/66 |
| 2003/0044995 A1 * | 3/2003 | Merabet et al. | 436/66 |

FOREIGN PATENT DOCUMENTS

| | | | |
|---|---|---|---|
| EP | 794435 | * | 9/1997 |
| WO | WO 95/24651 A1 | | 9/1995 |

OTHER PUBLICATIONS

Oshiro, I., et al., "New Method for Hemoglobin Determination by Using Sodium Lauryl Sulfate (SLS)", Clin. Biochem. 15(1), pp. 83-88 (1982).

* cited by examiner

*Primary Examiner*—Maureen M. Wallenhorst
(74) *Attorney, Agent, or Firm*—Cuspa Technology Law Associates; Mitchell E. Alter

(57) ABSTRACT

A cyanide-free lytic reagent composition and method of use for measuring the total hemoglobin concentration and white blood cells in a blood sample are disclosed. The lytic reagent composition includes a quaternary ammonium surfactant to lyse red blood cells and release hemoglobin and a ligand to form a stable chromogen with the hemoglobin. The lytic reagent composition has a pH in a range of 3 to 10. The lytic reagent composition can also include a second quaternary ammonium surfactant. The ligand can be malic acid, malonic acid, ethylene diamine, N,N-diethylethylene diamine, N,N'-diethylethylene diamine, diethylene triamine, tetraethylene pentamine, 1,6-hexanediamine, 1,3-pentanediamine, 2-methylpentamethylenediamine, 1,2-diaminocyclohexane, 4-aminoacetophenone, bis-hexamethylenetriamine, pyridazine, or 3,6-dihydroxypyridazine.

20 Claims, 3 Drawing Sheets

CYANIDE-FREE LYTIC REAGENT COMPOSITION AND METHOD OF USE FOR HEMOGLOBIN AND WHITE BLOOD CELL MEASUREMENT

FIELD OF THE INVENTION

The present invention relates to lytic reagent compositions and methods of use for measuring total hemoglobin concentration and white blood cells of a blood sample.

BACKGROUND OF THE INVENTION

The determination of total hemoglobin is indicative of the oxygen-carrying capacity of whole blood. More than 300 abnormal hemoglobins have been discovered upon examination of patients with clinical symptoms and by electrophoretic surveys of a clinically normal population. Many of these abnormalities result in clinical pathologies having altered hemoglobin levels or hemoglobin having an altered ability to bind oxygen. Among these diseases are sickle cell anemia, both $\alpha$ and $\beta$-thalassemias and hemoglobin M.

An ability to measure hemoglobin (Hgb) in blood samples is an essential part of diagnostic analysis and is also important for monitoring responsiveness to therapies directed towards diseases which affect hemoglobin and to therapies directed towards other diseases, which may have adverse side effects on the hemoglobin level.

White blood cells in the peripheral blood of normal subjects consist of five types, i.e., lymphocytes, monocytes, neutrophils, eosinophils and basophils. The latter three types of white blood cells are collectively referred to as granulocytes. Counting and differentiating different types of white blood cells in a blood sample provides valuable information for clinical diagnosis.

The classification and counting of white blood cells has most commonly been conducted by the differential analysis method which is also referred to as the manual method. Automatic blood analyzers are also commonly used for counting white blood cells, employing a lytic reagent to lyse red blood cells and then measuring the remaining white blood cells. A more sophisticated apparatus has been developed that counts different types of white blood cells (differential analysis of) including monocytes, lymphocytes and granulocytes. Ideally, one would like to be able to accomplish multiple diagnostic analyses such as hemoglobin measurement and counting the numbers of white blood cells or differential analysis of white blood cell subpopulations in a single automated step.

Among the many well-known methods for hemoglobin determination, the cyanide hemoglobin method has been recommended as a standard by the International Committee for Standardization in Hematology. Modification of this method by Matsubara and Okuzono has led to its wide usage in clinical laboratories. In this method, the iron ion of the heme group in all forms of hemoglobin of the red cells is oxidized to methemoglobin by potassium ferricyanide. The methemoglobin is then complexed with the cyanide anion, which has a very high affinity to the iron ion of the heme group, and forms a cyanmethemoglobin chromogen. This extremely stable chromogen has a maximum absorption at 540 nm, which is measured manually by spectrophotometer.

Despite the stable chromogens formed by the standard cyanmethemoglobin method and its modified automatic methods, the reagent waste has caused enormous environmental concern because of the potassium cyanide used. In the last twenty years, a tremendous effort has been undertaken to develop automated hemoglobin analysis methods without utilizing cyanide.

Oshiro et al, *Clin. Biochem.* 1583 (1982), teach the use of a reagent for hemoglobin analysis that comprises sodium laurylsulfate (SLS) and Triton X-100 (a nonionic surfactant) in a neutral pH (7.2). The SLS is used to lyse red blood cells and is believed to further produce a SLS-hemoglobin complex which has a maximum absorption at 539 nm and a shoulder at 572 nm. The reaction completes within 5-10 minutes and the total hemoglobin measurement is quantitative. However, as later taught in U.S. Pat. No. 5,242,832 (to Sakata), it is not possible with Oshiro's method to analyze white blood cells simultaneously with hemoglobin measurement.

U.S. Pat. No. 5,242,832 (to Sakata) discloses a cyanide-free lysing reagent for counting white blood cells and measuring the hemoglobin concentration in blood samples. The lysing reagent comprises at least one first surfactant which is a quaternary ammonium salt, at least one second surfactant which includes cationic and amphoteric surfactants, and at least one hemoglobin stabilizer selected from the group including Tiron, 8-hydroxyquinoline, bipyridine, 1-10-phenanthroline, phenolic compounds, bisphenol, pyrazole and derivatives, second phenyl 5-pyrazolone and derivatives, phenyl 3-pyrazolone, and imidazole and its derivatives. Sakata teaches that fractionation of the white blood cells into two or three groups including an aggregate of lymphocytes, an aggregate of monocytes, eosinophils and basophils, and an aggregate of neutrophils can only be accomplished by using at least two suitable surfactants and by rigorously controlling the surfactant concentration. Sakata also teaches that the preferred pH range of the lysing reagent is from 5.0 to 8.0. If the pH value is 3.0 or less, damage to the white blood cells increases thus rendering measurement of white blood cells difficult, and if the pH is 9.0 or more, the stability of hemoglobin deteriorates over time.

PCT/US95/02897 (Kim) discloses a cyanide-free reagent for determining hemoglobin in a whole blood sample. The reagent comprises a ligand selected from the group consisting of imidazole and derivatives, N-hydroxyacetamide, H-hydroxylamine, pyridine, oxazole, thiazole, pyrazole, pyrimidine, purine, quinoline and isoquinoline, and a surfactant with a strong erythrolytic capability selected from the group consisting of lauryl dimethylamine oxide and octylphenoxy polyethoxyethanol. The analysis method is fast, less than 10 seconds. However, the reagent only performs under an extreme alkaline condition, pH from 11 to 14. In addition, no capability of counting white blood cells or differentiating white blood cell subpopulations is taught by Kim.

U.S. Pat. Nos. 5,763,280 and 5,882,934 (to Li et al.) disclose cyanide-free reagents containing an organic ligand for measurement of hemoglobin and white blood cells in a blood sample. The organic ligand can be triazole and its derivatives, tetrazole and its derivatives, alkaline metal salts of oxonic acid, melamine, aniline-2-sulfonic acid, quinaldic acid, 2-amino-1,3,4-thiadiazole, triazine and its derivatives, urazole, DL-pipecolinic acid. isonicotinamide, anthranilonitrile, 6-aza-2-thiothymine, adenine, 3-(2-thienyl)acrylic acid, benzoic acid, alkali metal or ammonium salt of benzoic acid, or pyrazine and its derivatives.

U.S. Pat. No. 6,740,527 (to Wong et al.) discloses cyanide-free reagents for measurement of hemoglobin and white blood cells in a blood sample. The reagents contain at least one hydroxylamine salt selected from the group consisting of hydrochloride, sulfate, phosphate, and other acid salts.

A need is still present for a cyanide-free lytic reagent that contains a ligand that is inexpensive and environmentally friendly for a relatively large consumption on routine hematology analyzers.

SUMMARY OF THE INVENTION

In one aspect, the present invention is directed to a cyanide-free lytic reagent composition. The cyanide-free lytic reagent composition comprises an aqueous solution of: a quaternary ammonium surfactant, represented by the following molecular structure:

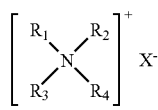

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide; and the quaternary ammonium surfactant is in an amount sufficient to lyse red blood cells and release hemoglobin; and a ligand in a sufficient amount to form a stable chromogen with the hemoglobin selected from the group consisting of: oxalic acid, malic acid, malonic acid, ethylene diamine, N,N-diethylethylene diamine, N,N'-diethylethylene diamine, diethylene triamine, tetraethylene pentamine, 1,6-hexanediamine, 1,3-pentanediamine, 2-methylpentamethylenediamine, 1,2-diaminocyclohexane, 4-aminoacetophenone, bis-hexamethylenetriamine, pyridazine, and 3,6-dihyroxypyridazine. The pH of the lytic reagent composition is in a range from about 3 to about 10. Preferably, the quaternary ammonium surfactant is dodecyl trimethyl ammonium chloride.

In another embodiment, the lytic reagent composition can further comprise a second quaternary ammonium surfactant. Preferably, the second quaternary ammonium surfactant is tetradecyl trimethyl ammonium bromide, or cetyldimethylethylammonium bromide.

In a further aspect, the present invention is directed to a method of measuring total hemoglobin concentration of a blood sample using the lytic reagent composition. The method comprises the steps of: diluting the blood sample with a blood diluent to form a diluted sample; mixing the diluted sample with the lytic reagent composition to form a sample mixture, the lytic reagent composition being in amount sufficient to lyse red blood cells and to form a stable hemoglobin chromogen in the sample mixture; measuring absorbance of the hemoglobin chromogen of the sample mixture at a predetermined wavelength; determining total hemoglobin concentration of the blood sample from the absorbance; and reporting the total hemoglobin concentration of the blood sample. Preferably, the absorbance is measured between about 510 nm and about 560 nm.

Moreover, the method further comprises the steps of counting numbers of white blood cells in the sample mixture on an automated blood analyzer using a first DC impedance measurement; and reporting the numbers of white blood cells of the blood sample. Additionally, the method can further comprise the steps of measuring sizes of the white blood cells in the sample mixture with a second DC impedance measurement in the automated blood analyzer and obtaining a size distribution histogram of the white blood cells; differentiating white blood cell subpopulations according to the distribution histogram; and reporting white blood cell subpopulations.

The invention and its various advantages will be better understood from the ensuing description of preferred embodiments, reference being made to the accompanying drawings.

DETAILED DESCRIPTION OF THE INVENTION

Figure 1:
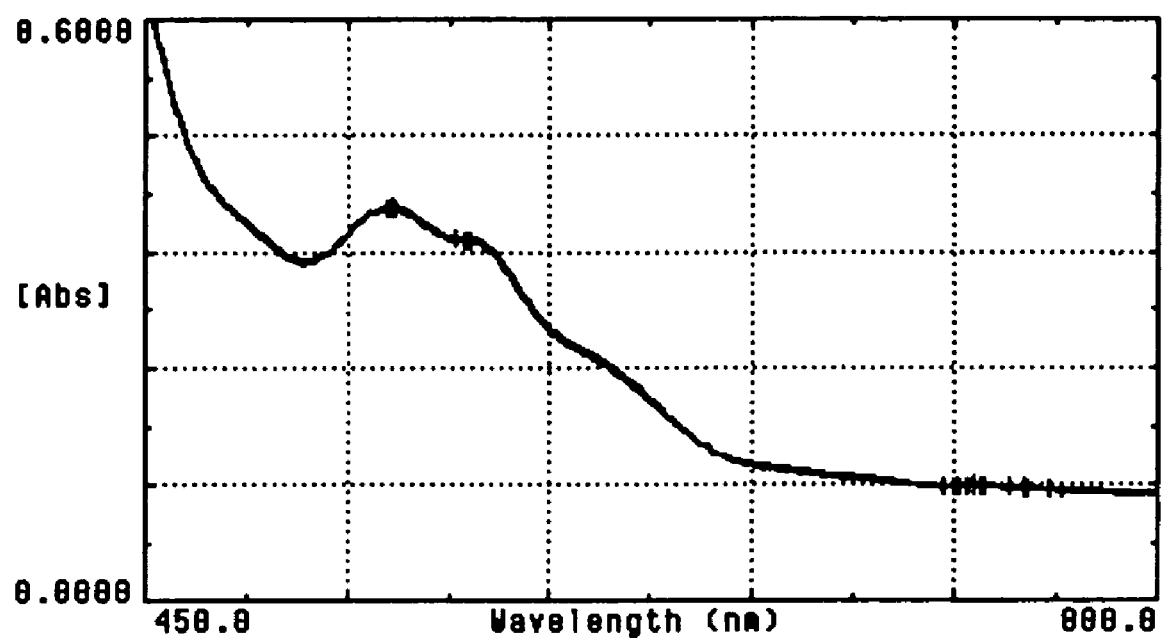
FIG. 1 shows a series of absorption spectra of a blood sample processed according to the procedure of Example 2 using the lytic reagent composition of Formula C of Example 2.

In one embodiment, the present invention provides a cyanide-free lytic reagent composition for measurement of the total hemoglobin concentration in a blood sample, and further for measurement of white blood cells of the blood sample. The cyanide-free lytic reagent composition comprises an aqueous solution of:

(i) a quaternary ammonium surfactant, represented by the following molecular structure:

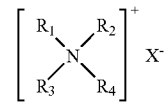

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide anion; and (ii) a ligand in a sufficient amount to form a stable chromogen with hemoglobin selected from the group consisting of:
(a) oxalic acid,
(b) malic acid,
(c) malonic acid,
(d) ethylene diamine,
(e) N,N-diethylethylene diamine,
(f) N,N'-diethylethylene diamine,
(h) diethylene triamine,
(i) tetraethylene pentamine,
(j) 1,6-hexanediamine,
(k) 1,3-pentanediamine,
(l) 2-methylpentamethylenediamine,
(m) 1,2-diaminocyclohexane,
(n) 4-aminoacetophenone,
(o) bis-hexamethylenetriamine,
(p) pyridazine, and
(r) 3,6-dihyroxypyridazine.

The pH of the lytic reagent composition is in a range from about 3 to about 10.

The lytic reagent composition can further comprise a second quaternary ammonium surfactant as represented by the molecular structure described above. In one preferred embodiment, the lytic reagent composition comprises a combination of dodecyl trimethyl ammonium chloride and tetradecyl trimethyl ammonium bromide. In another preferred embodiment, the lytic reagent composition comprises a combination of dodecyl trimethyl ammonium chloride and cetyl dimethylethyl ammonium bromide.

The concentration of the surfactant or combination of the surfactant in the lytic reagent composition is in an amount sufficient to lyse red blood cells and release hemoglobin, while preserving white blood cells for counting and measuring their size or volume. The concentration of the surfactants in the lytic reagent composition is in a range from about 2 g/L to about 100 g/L, preferably, from about 4 g/L to about 60 g/L.

When a blood sample is mixed with the lytic reagent composition described above, the red blood cells are completely lysed, and hemoglobins are released to the sample mixture, which upon contacting with the ligand in the lytic reagent composition forms a stable chromogen. The hemoglobin chromogen can be measured by UV-VIS spectroscopy at a predetermined wavelength. On the other hand, upon mixing with the lytic reagent composition, the cellular membrane of the white blood cells is permeated and the cytoplasm is substantially released, however, the nuclei are preserved. The remaining white blood cells can be measured by a direct current (DC) impedance measurement for the purpose of counting or differential analysis of white blood cell subpopulations.

The hemoglobins released upon lysing the red blood cells include various forms, such as oxyhemoglobin, deoxyhemoglobin, methemoglobin, carboxyhemoglobin, etc. For the measurement to be quantitative and accurate, the formed chromogen needs to be stable during the time period of the measurement. The most efficient method to convert hemoglobin to a stable chromogen is to provide a ligand which has a high affinity to the heme iron and forms a stable hemoglobin complex. This has been successfully demonstrated by the cyanmethemoglobin method, wherein the cyanide anion has an extremely high affinity to the heme iron. The terms "hemoglobin complex" and "hemoglobin chromogen" are used herein interchangeably. Usually, in the absence of a high affinity ligand, the formed hemoglobin chromogen may not be sufficiently stable. The absorption of the chromogen varies, and in most cases decays with time. Under this condition, the method of analysis is unreliable even if the kinetics of the reaction is well monitored and corrected, because the chromogen could be very sensitive to various environmental factors, such as temperature and sample preparation conditions. When an appropriate hemoglobin ligand is provided, the hemoglobin conversion can be quantitative, and a reliable measurement of the total hemoglobin concentration of the blood sample can be ensured by the stability of the formed hemoglobin chromogen.

It has been found that the ligands described above can effectively convert the hemoglobins into a stable chromogen during the time commonly used on a blood analyzer. The concentration of the ligand in the lytic reagent composition is in amount sufficient to form a stable hemoglobin chromogen. The concentration varies with the specific ligand used, depending on the affinity of the ligand to the hemoglobin. If the amount of ligand in the lytic reagent composition is not sufficient, the formed hemoglobin chromogen could be unstable. The concentration of the ligand in the lytic reagent composition of the present invention is in a range from about 0.3 g/L to about 25.0 g/L, preferably from about 5.0 g/L to about 20.0 g/L.

The concentrations of the surfactants and the ligand of the lytic reagent composition described above are the concentrations wherein the measurements of hemoglobin and white blood cells are accomplished with the use of a suitable blood diluent in the sample preparation. However, the concentrations of these components described above can be adjusted, depending upon the volume ratio between the lytic reagent composition and the diluent used for preparing the sample mixture.

Moreover, if a blood analyzer employs a single lytic reagent composition, without predilution by a blood diluent, one can reduce the concentrations of the surfactants and the ligands of the lytic reagent composition and adjust the conductivity of the lytic reagent composition to enable its use for impedance measurements. The conductivity can be adjusted by the addition of suitable amounts of alkaline metal salts. In this type of single reagent method, the concentrations of the surfactants and the ligands in the lytic reagent composition should be the same as the concentrations contained in the final sample mixture when both a diluent and a lytic reagent composition are used.

Optional additives can also be included in the lytic reagent composition of the present invention in concentrations that their presence is compatible with the primary functional components of the lytic reagent composition. Among these additives are preservatives that have anti-oxidant properties to increase the shelf-life of the composition, and that have anti-microbial properties.

Example 1 illustrates two examples of the cyanide-free lytic reagent composition of the present invention.

In a further embodiment, the present invention provides a method of using the cyanide-free lytic reagent composition described above for measuring the total hemoglobin concentration in a blood sample. The method comprises the steps of: diluting a blood sample with a blood diluent to form a diluted sample; mixing the diluted sample with the lytic reagent composition to form a sample mixture and to lyse red blood cells and form a stable hemoglobin chromogen in the sample mixture; measuring absorbance of the hemoglobin chromogen of the sample mixture at a predetermined wavelength; determining total hemoglobin concentration of the blood sample from the obtained absorbance; and reporting the total hemoglobin concentration of the blood sample. The absorbance of the blood sample is measured between about 510 nm and about 560 nm.

In a preferred embodiment, the method further comprises counting numbers of white blood cells, and differentiating white blood cell subpopulations in the sample mixture using DC impedance measurements on an automated blood analyzer.

The detection methods used for counting white blood cells by a blood analyzer equipped with a DC impedance measurement device are generally described in U.S. Pat. No. 2,656,508, which is hereby incorporated by reference in its entirety. The method of differentiating white blood cell subpopulations using a DC impedance measurement is described in U.S. Pat. Nos. 4,485,175 and 4,528,274, which are hereby incorporated by reference in their entireties.

The process of measurement of the total hemoglobin of a blood sample using the lytic reagent composition of the present invention is described in general here, which is further illustrated in detail in Example 2 hereinafter. An anti-coagulated blood sample is diluted by a suitable blood diluent, then a sufficient amount of lytic reagent composition described above is mixed with the diluted sample by manual or mechanical mixing to form a sample mixture. The dilution ratio of the blood is from about 125:1 to about 500:1, the total reagent volume versus the blood sample. The sample mixture is measured photometrically, from about 10 to 60 seconds after the addition of the lytic reagent composition, either on a spectrometer or on an automated blood analyzer equipped with a photo-detector at a predetermined absorption wavelength. The blood analyzer can be further equipped with a DC impedance measurement device to count the numbers of white blood cells, or to further differentiate the white blood cell subpopulations based on the population distribution histogram obtained. In the later case, the white blood cells are differentiated into two or more subpopulations, including lymphocytes, monocytes and granulocytes.

The blood diluent can be used with the lytic reagent composition of the present invention is an isotonic diluent, which is commonly used on commercial hematology analyzer for diluting blood samples. Suitable examples include, but are not limited to, the diluents described in U.S. Pat. Nos. 4,521,518, 4,528,274, 5,935,857 and 6,706,526, which are hereby incorporated by reference in their entireties.

FIG. 1 shows a series of absorption spectra of a blood sample processed according to the procedure of Example 2 using the lytic reagent composition of Formula C of Example 2, and COULTER® ISOTON® 3E (a commercial blood diluent manufactured by Beckman Coulter, Inc. Miami, Fla.) as the diluent. FIG. 1 illustrates a total of 12 spectra acquired from 12 seconds to 132 seconds after the addition of the lytic reagent composition with an interval of 10 seconds. The spectra of the hemoglobin chromogen are very stable and exhibit no shift or decay during the test period of 120 seconds.

Most chromogens formed by using the lytic reagent composition of the present invention with the ligands described above have their maximum absorptions between about 510 nm and about 560 nm. Therefore, the chromogens can be measured by most commercial blood analyzers with incorporation of the absorption coefficient of the specific chromogen.

Figure 2:
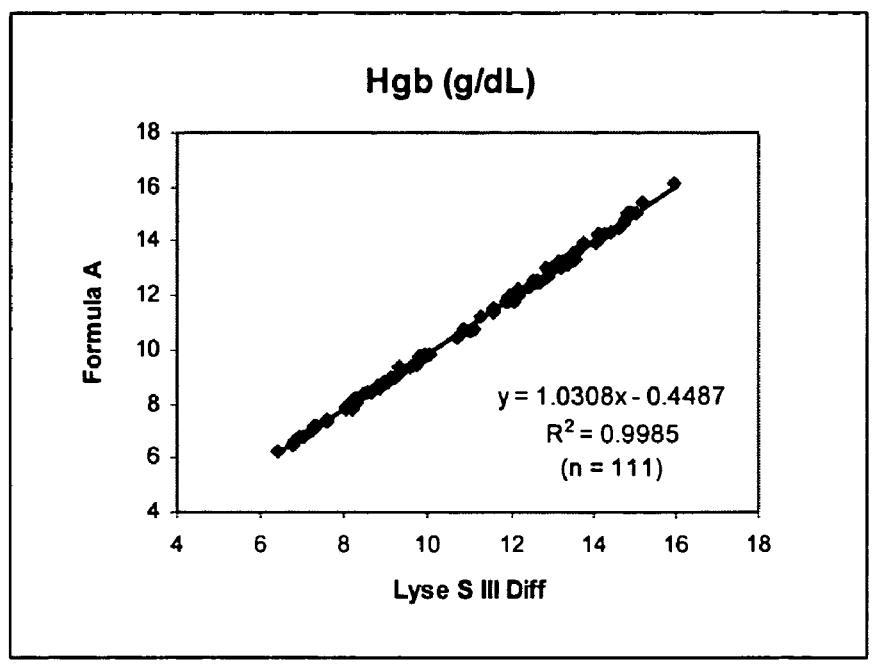
FIG. 2 shows the correlation of the hemoglobin concentration between the results obtained using Formula A and the results obtained on the reference instrument.
Figure 3:
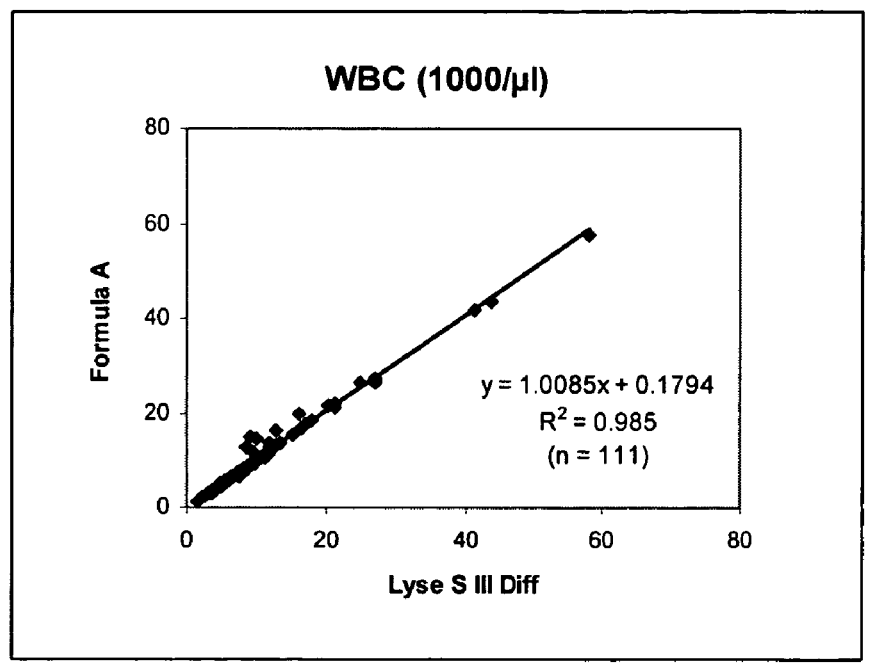
FIG. 3 shows the correlation of the numbers of white blood cells (reported as WBC in $10^3/\mu L$) between the results obtained using Formula A and the results obtained on the reference instrument.

The lytic reagent composition of the present invention and the method of using the same provide an accurate hemoglobin measurement and accurate count of white blood cells. FIG. 2 shows an excellent linear correlation between the hemoglobin concentrations obtained on a COULTER® LH750 hematology analyzer (a product of Beckman Coulter, Inc., Miami, Fla.) using a conventional lytic reagent and the hemoglobin concentrations obtained using Formula A of Example 1. FIG. 3 illustrates excellent correlation between the white blood cell count obtained on the COULTER® LH750 hematology analyzer using the conventional lytic reagent and the results obtained using Formula A of Example 1 on the same instrument.

The following examples are illustrative of the invention and are in no way to be interpreted as limiting the scope of the invention, as defined in the claims.

EXAMPLE 1

The following lytic reagent compositions were prepared.

| Formula A | |
|---|---|
| 1,2-diaminocyclohexane | 10.0 g |
| dodecyltrimethylammonium chloride (50% solution) | 35.6 g |
| cetyldimethylethylammonium bromide | 1.25 g |
| distilled water adjusted to 1 liter | |
| pH | 5.5 |

| -continued | |
|---|---|
| Formula B | |
| 3,6-dihyroxypyridazine | 10.0 g |
| dodecyltrimethylammonium chloride (50% solution) | 50.0 g |
| tetradecyltrimethylammonium bromide | 3.5 g |
| distilled water adjusted to 1 liter | |
| pH | 6.0 |

EXAMPLE 2

| Formula C | |
|---|---|
| 1,2-diaminocyclohexane | 16.8 g |
| dodecyltrimethylammonium chloride (50% solution) | 35.5 g |
| cetyldimethylethylammonium bromide | 2.0 g |
| distilled water adjusted to 1 liter | |
| pH | 5.5 |

11.6 µl of a whole blood sample was diluted by 2500 µl of ISOTON® 3E, then 403 µl of a lytic reagent composition of Formula C was mixed manually with the prediluted sample. The absorption spectrum of the sample mixture was measured immediately on a Beckman DU 7500 spectrophotometer. FIG. 1 shows a total of 12 spectra of the blood samples treated according to above procedure using Formula C. The spectra were acquired from 12 seconds after the addition of the lytic reagent composition with an interval of 10 seconds.

EXAMPLE 3

111 blood samples, their hemoglobin concentration ranging from 6 to 17 g/dL and white blood cell count ranging from 1,000 µL to 40,000 µL, were analyzed on a calibrated COULTER® LH750 instrument under standard instrument configuration except for the lytic reagent being replaced by Formula A. These sample were also analyzed on another reference LH750 instrument, which used LYSE S® III diff as the lytic reagent. More than 50 percent of the samples were clinical samples including various clinical conditions.

FIG. 2 shows the correlation of the hemoglobin concentration between the results obtained using Formula A and the results obtained on the reference instrument. FIG. 3 shows the correlation of the numbers of white blood cells (reported as WBC in $10^3/\mu L$) between the results obtained using Formula A and the results obtained on the reference instrument.

Figure 4A:
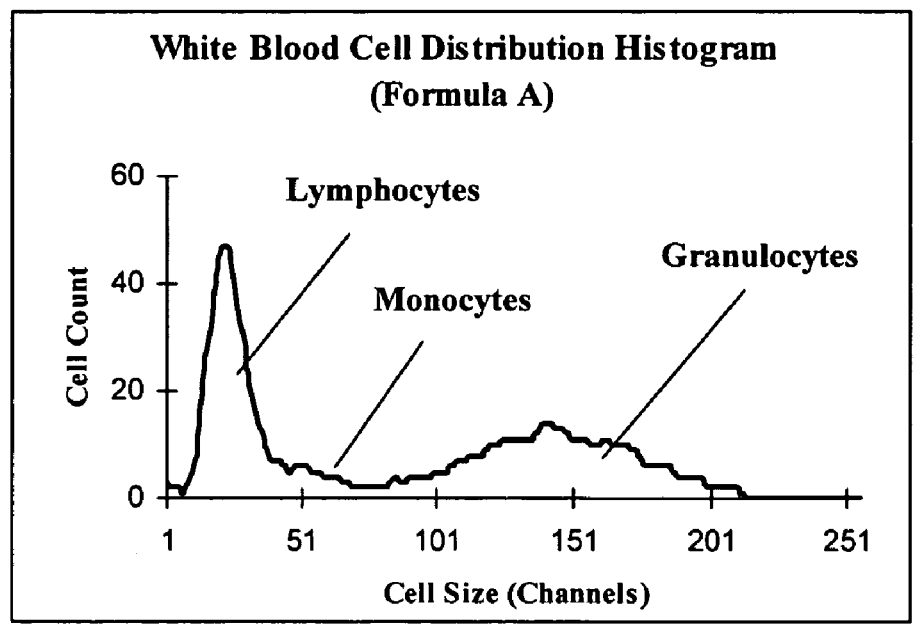
FIGS. 4A and 4B show the white blood cell distribution histograms of one blood sample obtained on the instrument using Formula A and the reference instrument, respectively.
Figure 4B:
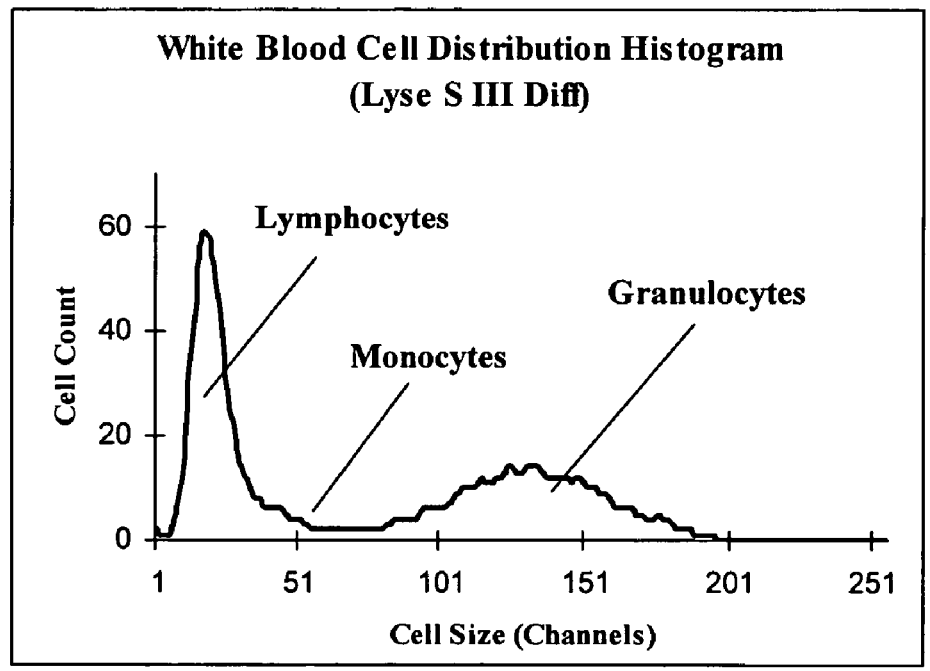

FIGS. 4A and 4B show the white blood cell distribution histograms of one blood sample obtained on the instrument using Formula A and the reference instrument, respectively. As shown, using Formula A, similar to the white blood cell distribution obtained using the reference reagent, LYSE S® III diff, the white blood cells were differentiated into lymphocytes, monocytes and granulocytes.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A cyanide-free lytic reagent composition comprising an aqueous solution of:
   (i) a quaternary ammonium surfactant, represented by following molecular structure:

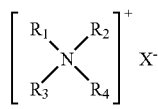

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide; and said quaternary ammonium surfactant is in an amount sufficient to lyse red blood cells and release hemoglobin; and
   (ii) a ligand in a sufficient amount to form a stable chromogen with said hemoglobin selected from the group consisting of:
   (a) oxalic acid,
   (b) malic acid,
   (c) malonic acid,
   (d) ethylene diamine,
   (e) N,N-diethylethylene diamine,
   (f) N,N'-diethylethylene diamine,
   (h) diethylene triamine,
   (i) tetraethylene pentamine,
   (j) 1,6-hexanediamine,
   (k) 1,3-pentanediamine,
   (l) 2-methylpentamethylenediamine,
   (m) 1,2-diaminocyclohexane,
   (n) 4-aminoacetophenone,
   (o) bis-hexamethylenetriamine,
   (p) pyridazine, and
   (r) 3,6-dihyroxypyridazine;
   wherein pH of said lytic reagent composition is in a range from about 3 to about 10.

2. The lytic reagent composition of claim 1, wherein said quaternary ammonium surfactant has a concentration in a range from about 4 g/L to about 60 g/L.

3. The lytic reagent composition of claim 1, wherein said ligand is in a concentration range from about 0.3 g/L to about 25.0 g/L.

4. A method of measuring total hemoglobin concentration of a blood sample using said lytic reagent composition of claim 1 comprising:
   (a) diluting said blood sample with a blood diluent to form a diluted sample;
   (b) mixing said diluted sample with said lytic reagent composition of claim 1 to form a sample mixture, said lytic reagent composition being in amount sufficient to lyse red blood cells and to form a stable hemoglobin chromogen in said sample mixture;
   (c) measuring absorbance of said hemoglobin chromogen of said sample mixture at a predetermined wavelength;
   (d) determining total hemoglobin concentration of said blood sample from said absorbance obtained in step (c); and
   (e) reporting said total hemoglobin concentration of said blood sample.

5. The method of claim 4, wherein said absorbance is measured between about 510 nm and about 560 nm.

6. The method of claim 4 further comprising the steps of:
   counting numbers of white blood cells in said sample mixture in an automated blood analyzer using a first DC impedance measurement; and
   reporting said numbers of white blood cells of said blood sample.

7. A cyanide-free lytic reagent composition comprising an aqueous solution of:
   (i) two quaternary ammonium surfactants, represented by following molecular structure:

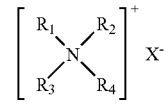

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide; and
   (ii) a ligand in a sufficient amount to form a stable chromogen with hemoglobin selected from the group consisting of:
   (a) oxalic acid,
   (b) malic acid,
   (c) malonic acid,
   (d) ethylene diamine,
   (e) N,N-diethylethylene diamine,
   (f) N,N'-diethylethylene diamine,
   (h) diethylene triamine,
   (i) tetraethylene pentamine,
   (j) 1,6-hexanediamine,
   (k) 1,3-pentanediamine,
   (l) 2-methylpentamethylenediamine,
   (m) 1,2-diaminocyclohexane,
   (n) 4-aminoacetophenone,
   (o) bis-hexamethylenetriamine,
   (p) pyridazine, and
   (r) 3,6-dihyroxypyridazine;
   wherein pH of said lytic reagent composition is in a range from about 3 to about 10; and said surfactants are in amounts sufficient to lyse red blood cells, release hemoglobin, while preserve white blood cells for counting and differential analysis.

8. The lytic reagent composition of claim 7, wherein said ligand is in a concentration range from about 0.3 g/L to about 25.0 g/L.

9. The lytic reagent composition of claim 7, wherein a first quaternary ammonium surfactant is dodecyl trimethyl ammonium chloride.

10. The lytic reagent composition of claim 9, wherein said dodecyl trimethyl ammonium chloride is in a concentration range from about 30 g/L to about 60 g/L.

11. The lytic reagent composition of claim 7, wherein a second quaternary ammonium surfactant is tetradecyl trimethyl ammonium bromide.

12. The lytic reagent composition of claim 7, wherein a second surfactant is cetyldimethylethylammonium bromide.

13. A method of measuring total hemoglobin concentration of a blood sample using said lytic reagent composition of claim 7 comprising:
   (a) diluting said blood sample with a blood diluent to form a diluted sample;
   (b) mixing said diluted sample with said lytic reagent composition of claim 7 to form a sample mixture, said lytic reagent composition being in amount sufficient to lyse red blood cells and to form a stable hemoglobin chromogen in said sample mixture;

(c) measuring absorbance of said hemoglobin chromogen of said sample mixture at a predetermined wavelength;

(d) determining total hemoglobin concentration of said blood sample from said absorbance obtained in step (c); and (e) reporting said total hemoglobin concentration of said blood sample.

14. The method of claim 13, wherein said absorbance is measured between about 510 nm and about 560 nm.

15. The method of claim 13 further comprising the steps of:
counting numbers of white blood cells in said sample mixture in an automated blood analyzer using a first DC impedance measurement; and
reporting said numbers of white blood cells of said blood sample.

16. The method of claim 15 further comprising the steps of:
measuring sizes of said white blood cells in said sample mixture with a second DC impedance measurement in said automated blood analyzer and obtaining a size distribution histogram of said white blood cells;
differentiating white blood cell subpopulations according to said distribution histogram; and
reporting white blood cell subpopulations.

17. The method of claim 16, wherein said white blood cell subpopulations are two or more populations selected from the group consisting of lymphocytes, monocytes and granulocytes.

18. A cyanide-free lytic reagent composition comprising an aqueous solution of:

(i) two quaternary ammonium surfactants, represented by following molecular structure:

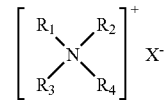

wherein $R_1$ is an alkyl, alkenyl or alkynyl group having 10 to 18 carbon atoms; $R_2$, $R_3$ and $R_4$ are alkyl groups having 1 to 4 carbon atoms and $X^-$ is chloride or bromide; and (ii) a ligand in a sufficient amount to form a stable chromogen with said hemoglobin selected from the group consisting of 1,2-diaminocyclohexane, and 3,6-dihydroxypyridazine;

wherein pH of said lytic reagent composition is in a range from about 3 to about 10; and said surfactants are in amounts sufficient to lyse red blood cells, release hemoglobin, while preserve white blood cells for counting and differential analysis.

19. The lytic reagent composition of claim 18, wherein a first quaternary ammonium surfactant is dodecyl trimethyl ammonium chloride.

20. The lytic reagent composition of claim 19, wherein a second quaternary ammonium surfactant is tetradecyl trimethyl ammonium bromide or cetyldimethylethylammonium bromide.

* * * * *